(12) United States Patent
Tyagi et al.

(10) Patent No.: US 8,309,723 B2
(45) Date of Patent: Nov. 13, 2012

(54) PREPARATION OF ZOPICLONE AND ITS ENANTIOMERICALLY ENRICHED ISOMER

(75) Inventors: Om Dutt Tyagi, Hyderabad (IN); Tushar Kumar Srivastava, Hyderabad (IN); Vellanki Siva Ram Prasad, Hyderabad (IN); Dnyandev Ragho Rane, Hyderabad (IN); Bandi Naga Durga Rao, Hyderabad (IN); Daggula Srinivas Reddy, Hyderabad (IN)

(73) Assignee: Mylan Laboratories Ltd., Hyderabad (IN)

( * ) Notice: Subject to any disclaimer, the term of this patent is extended or adjusted under 35 U.S.C. 154(b) by 280 days.

(21) Appl. No.: 12/595,663

(22) PCT Filed: Apr. 10, 2008

(86) PCT No.: PCT/IN2008/000239
§ 371 (c)(1),
(2), (4) Date: Oct. 13, 2009

(87) PCT Pub. No.: WO2008/126105
PCT Pub. Date: Oct. 23, 2008

(65) Prior Publication Data
US 2010/0056785 A1    Mar. 4, 2010

(30) Foreign Application Priority Data
Apr. 12, 2007 (IN) .............................. 782/CHE/2007

(51) Int. Cl.
*C07D 495/00* (2006.01)

(52) U.S. Cl. .................. 544/350; 544/389; 546/345
(58) Field of Classification Search .................. 544/350, 544/389; 546/345
See application file for complete search history.

(56) References Cited

FOREIGN PATENT DOCUMENTS
WO    WO 2008/126105    * 10/2008

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*

* cited by examiner

*Primary Examiner* — Douglas M Willis
(74) *Attorney, Agent, or Firm* — Ladas & Parry LLP

(57) ABSTRACT

Present invention relates to an improved process for the preparation of Zopiclone and its enantiomerically enriched isomer (Eszopiclone). 6-(5-Chloropyridin-2-yl)-5-hydroxy-7-oxo-5,6-dihydropyrrolo[3,4-b]pyrazine is reacted with 1-chloro-carbonyl-4-methylpiperazine in the presence of alkali earth metal carbonates, hydroxides or oxides in a solvent medium to give Zopiclone. It is reacted with optically active acid in a mixture of water and water miscible organic solvent followed by work up to give Eszopiclone. The present invention also relates to process for the conversion of (R) or (S) Zopiclone to 6-(5-chloropyrid-2-yl)-5-hydroxy-7-oxo-5, 6-dihydro-pyrrolo-[3,4-b]-pyrazine of the intermediate which can be converted to racemic Zopiclone.

7 Claims, 2 Drawing Sheets

PREPARATION OF ZOPICLONE AND ITS ENANTIOMERICALLY ENRICHED ISOMER

FIELD OF INVENTION

Present invention relates to an improved process for the preparation of therapeutically useful 6-(5-chloropyridin-2-yl)-7-oxo-6,7-dihydro-5H-pyrrolo[3,4b]pyrazin-5-yl4-methyl piperazine-1-carboxylate (Zopiclone) and it's enantiomerically enriched isomer (Eszopiclone). The process is industrially advantageous and provides improved yield and purity with less number of synthetic steps.

BACKGROUND OF THE INVENTION

Zopiclone a cyclopyrrolone derivative, belonging to a novel chemical class which is structurally unrelated to existing hypnotics chemically named as (±) 6-(5-chloropyridin-2-yl)-7-oxo-6,7-dihydro-5H-pyrrolo[3,4b]pyrazin-5-yl4-methyl piperazine-1-carboxylate of formula (I).

Formula I

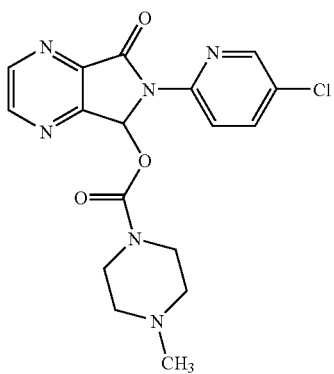

Eszopiclone represented by formula II and is the S-isomer of racemic product Zopiclone. Eszopiclone is found to be more specific for the GABA binding sites and possesses an approximately 50-fold higher binding affinity to GABA-A receptors than the R-Isomer. Also the hypnotic activity of S-Zopiclone is reported to be two folds more than racemic Zopiclone Formula II

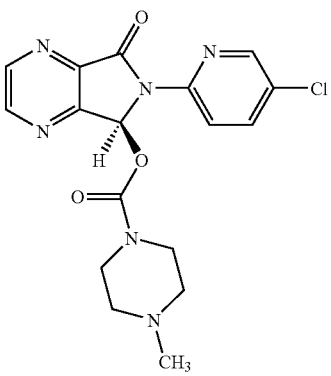

U.S. Pat. NO. 3,862,149 patent discloses the process for the preparation of Zopiclone, wherein 6-(5-chloropyridin-2-yl)-5-hydroxy-7-oxo-5,6-dihydro pyrrolo-[3,4-b]-pyrazine is condensed with 1-chlorocarbonyl-4-methyl-piperazine in the presence of strong base such as sodium hydride in dimethylformamide to give Zopiclone. According to the prior art process, sodium hydride is used for condensation reaction, handling sodium hydride in the plant level needs lot of safety precautions.

U.S. Pat. No. 6,319,926 patent discloses the process for the preparation of Eszopiclone, wherein (±)-Zopiclone is converted into diastereomeric salts using D(+)-O,O'-dibenzoyltartaric acid in dichloromethane followed by concentration to give crude residue. Crude residue is recrystallised in acetonitrile to obtain solid, which is further subjected to second purification by dissolving in dichloromethane at reflux temperature followed by addition of acetonitrile to give pure salt an over all yield of only 23%.

U.S. Pat. No. 6,339,086 teaches process for the preparation of Eszopiclone, whereas (±)-Zopiclone is converted into diastereomeric salts using D-malic acid in a mixture of acetone and methanol followed by work up to obtain Eszopiclone in an over all yield of 36%.

ES 2,101,653 discloses an enzymatic resolution of racemic mixture of compounds to yield optically pure Eszopiclone.

According to the prior art, processes need repeated crystallization in different solvents to get desired quality of the diastereomeric salt. It leads to yield loss and increase in the raw material cost.

Hence there still exists a need for development of feasible and industrially viable process for synthesis of Zopiclone. The present invention provides the process to prepare therapeutically active enantiomerically enriched isomer of Eszopiclone with improved yield, which is industrially applicable, non-hazardous and less expensive.

SUMMARY OF THE INVENTION

The main aspect of the present invention is to provide a novel process for the preparation of Eszopiclone.

Another aspect of the present invention is to provide a process for the preparation of enantiomerically enriched isomer of Eszopiclone with chiral purity of about 95 to 99.5%

Yet another aspect of the present invention is to provide a process for the resolution of racemic Zopiclone to give Eszopiclone with improved yield.

A further aspect of the present invention is to provide improved process for the preparation of Zopiclone.

Still another aspect of the present invention is to provide process for the conversion of (R) or (S) Zopiclone to 6-(5-chloropyridin-2-yl)-5-hydroxy-7-oxo-5,6-dihydro pyrrolo-[3,4-b]-pyrazine of the intermediate which can be converted to racemic Zopiclone.

POWDER X-RAY DIFFRACTION (PXRD)

Figure 1:
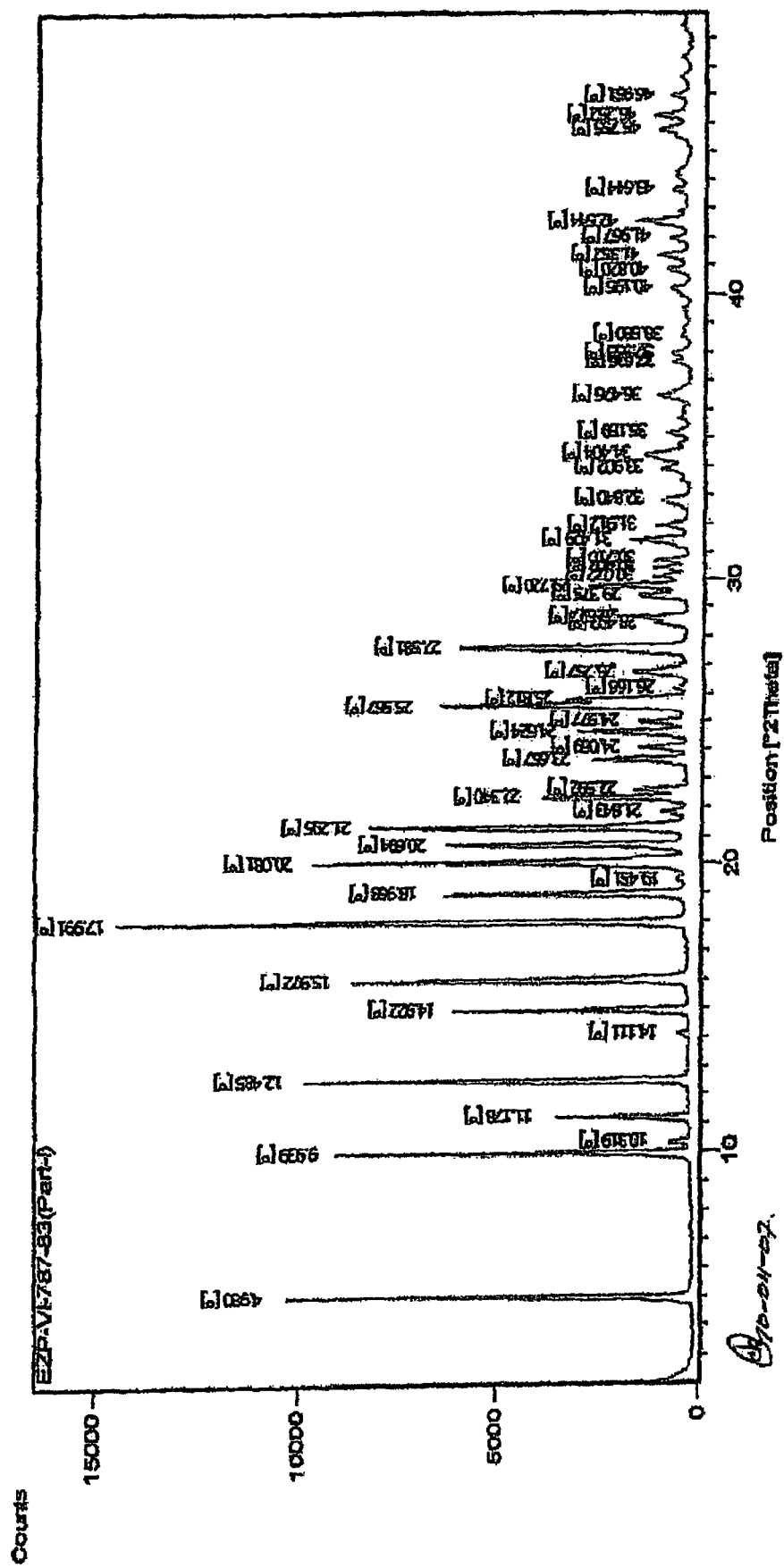
FIG. 1: X-ray diffraction pattern of the Eszopiclone (purity~99%)
Figure 2:
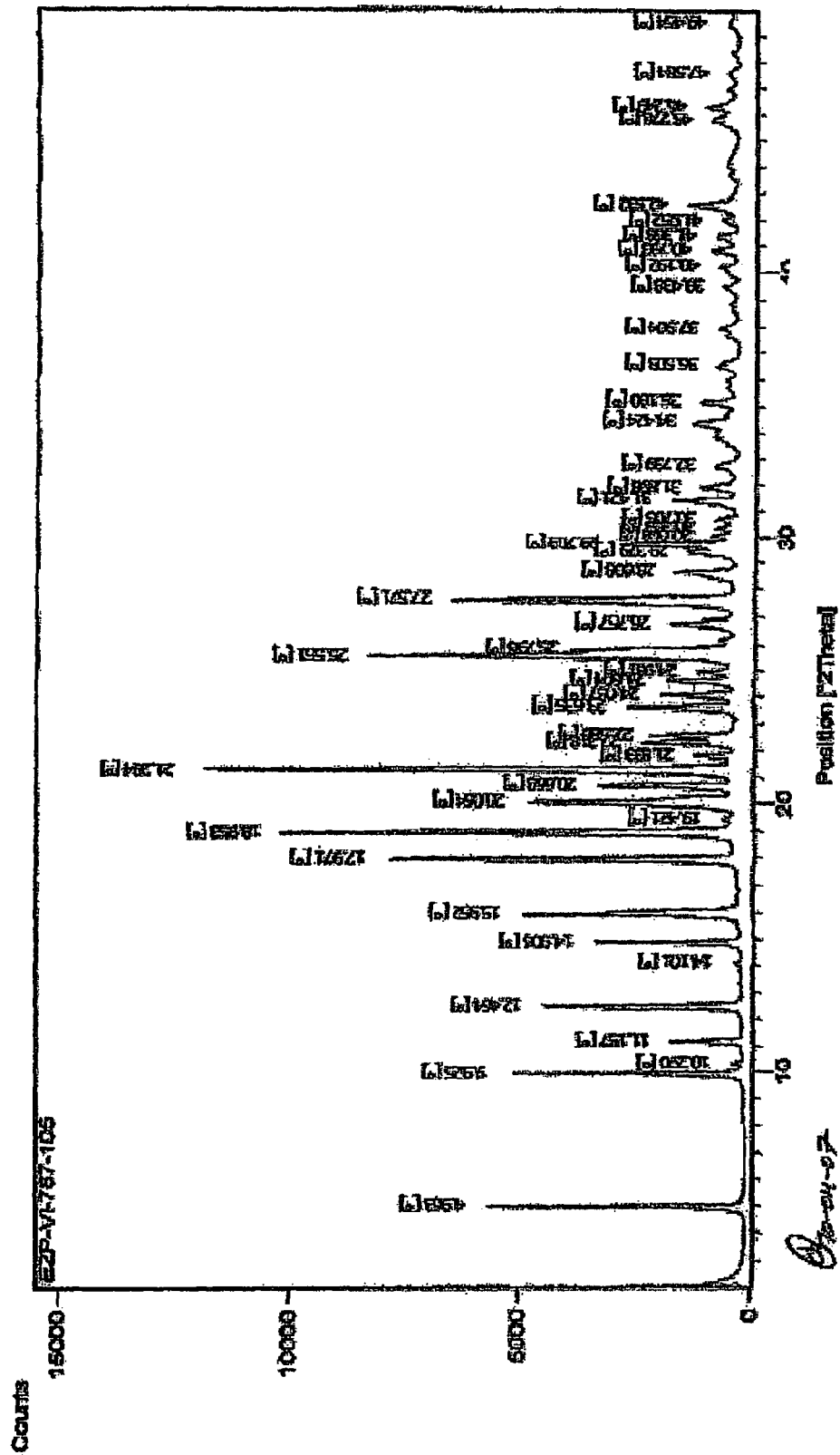
FIG. 2: X-ray diffraction pattern of the Eszopiclone (purity~97.5%)

The said polymorphs of the present invention are characterized by their X-ray powder diffraction pattern. Thus, the X-ray diffraction patterns of said polymorphs of the invention were measured on PANalytical, X'Pert PRO powder diffractometer equipped with goniometer of θ/θ configuration and X'Celerator detector. The Cu-anode X-ray tube was operated at 40 kV and 30 mA. The experiments were conducted over the 2θ range of 2.0°-50.0°, 0.030° step size and 50 seconds step time.

DETAILED DESCRIPTION OF THE INVENTION

The present invention relates to an improved process for the preparation of therapeutically useful (Zopiclone) and its enantiomerically enriched isomer (Eszopiclone). 6-(5-Chloropyridin-2-yl)-5-hydroxy-7-oxo-5,6-dihydropyrrolo [3,4-b] pyrazine is reacted with 1-chlorocarbonyl-4-methylpiperazine in the presence of dimethylaminopyridine and alkali earth metal carbonates, hydroxides or oxides in a solvent medium to give Zopiclone. It is reacted with optically active acid in a mixture of water and water miscible organic solvent followed by work up to give Eszopiclone. The present invention also relates to process for the conversion of (R) or (S) Zopiclone to 6-(5-chloropyridin-2-yl)-5-hydroxy-7-oxo-5,6-dihydropyrrolo-[3,4-b]-pyrazine of the intermediate which can be converted to racemic Zopiclone.

An improved process for the preparation of Esopiclone comprising the steps of:

According to our present invention, condensation of 6-(5-chloropyridin-2-yl)-5-hydroxy-7-oxo-5,6-dihydropyrrolo[3, 4-b]pyrazine with 1-chlorocarbonyl-4-methylpiperazine in the presence of dimethylaminopyridine (DMAP) and alkali earth metal carbonates, hydroxides or oxides in a solvent medium to give Zopiclone. The alkali earth metal carbonate is selected from magnesium carbonate, calcium carbonate; alkaline earth metal hydroxide is selected from magnesium hydroxide, calcium hydroxide; Alkaline earth metal oxide is magnesium oxide, calcium oxide. The preferred alkaline earth metal oxide is calcium oxide.

According to the present invention, condensation reaction is carried out in a solvent selected from toluene, dichloromethane, dichloroethane, ethylacetate, tetrahydrofuran, N,N'-dimethylformamide, N,N'-dimethylacetamide, dimethyl sulfoxide or mixtures thereof; The preferred solvent is mixture of dichloromethane and dimethylformamide.

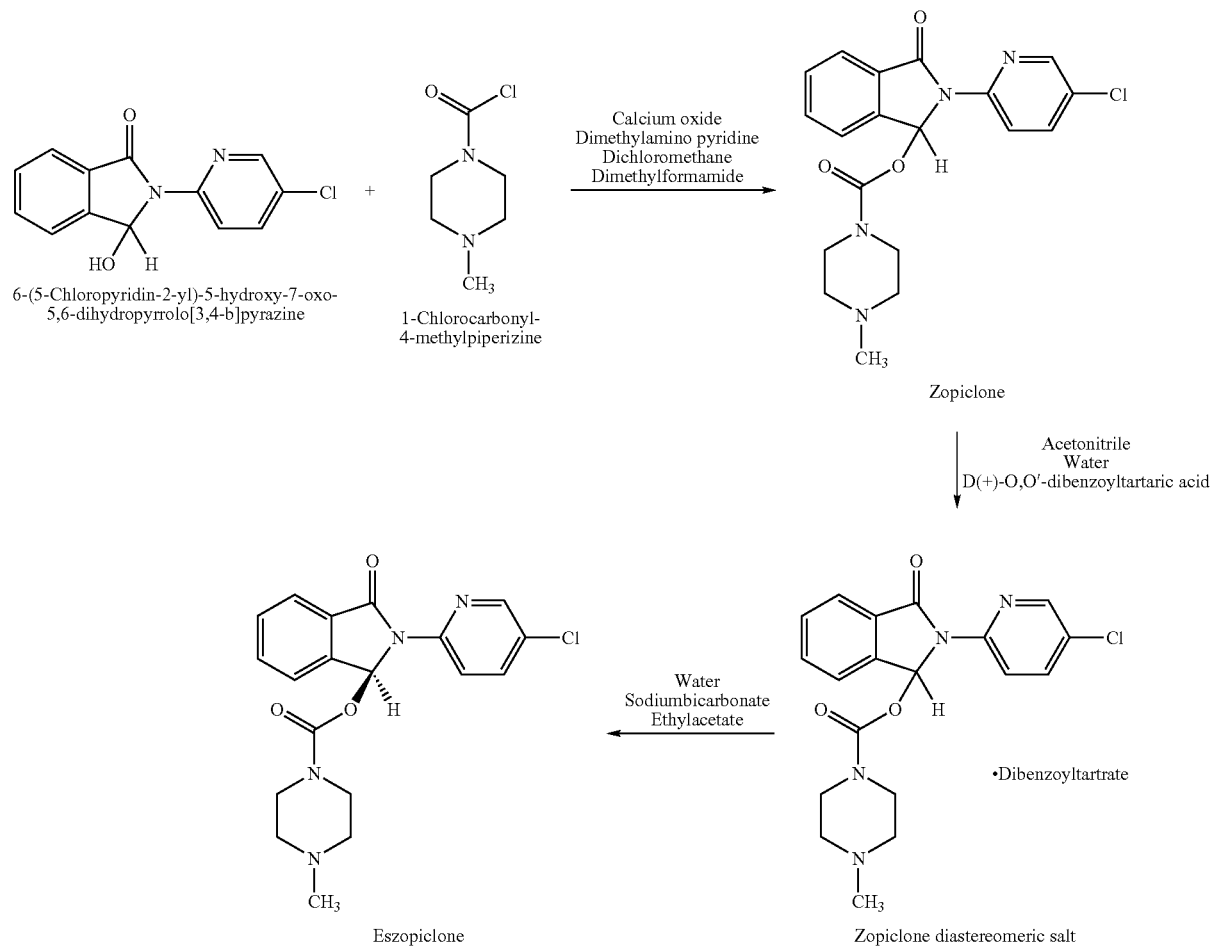

(a) condensing 6-(5-chloropyridin-2-yl)-5-hydroxy-7-oxo-5,6-dihydropyrrolo [3,4-b] pyrazine with 1-chlorocarbonyl-4-methylpiperazine in the presence of dimethylaminopyridine and alkaline earth metal carbonates, hydroxides or oxides in a solvent medium to give Zopiclone.

(b) reacting Zopiclone with optically active acid in a mixture of water and water miscible organic solvent and recovering Eszopiclone.

As per the prior art process condensation reaction is carried out in the presence of strong base such as sodium hydride. Handling the sodium hydride in commercial scale requires more safety precaution due to fire hazards. According to our present invention sodium hydride base is replaced with hazards free calcium oxide.

Another aspect of the present invention relates to reacting Zopiclone with optically active acid in a mixture of water and water miscible organic solvent and recovering R or S-Zopiclone. The optically active acid is selected from D (+)-O,O'-dibenzoyltartaric acid, D (+)-O,O'-p-toloyldibenzoyltartaric acid or D (+) mandelic acid; the preferred optically active acid is D (+)-O,O'-dibenzoyltartaric acid.

According to our present invention resolution reaction is carried out in a mixture of water and water miscible organic solvent. Water miscible organic solvent is selected from ketone, nitrile and aprotic polar solvents. The selected ketone solvent is acetone, nitrine solvent is acetonitrile or propionitrile, aprotic polar solvent is N,N'-dimethylformamide, N,N'-dimethylacetamide or dimethyl sulfoxide. The preferred water miscible organic solvent is acetonitrile.

As per the prior art process resolution reaction is carried out in a single solvent to obtain diastereomeric salt, which is further subjected to number of purification in different solvents or mixture of solvents to get the desired quality of the salt. According to our present invention resolution is carried out in a mixture of water and water miscible organic solvent to get desired quality of diastereomeric salt, without subjecting the purification.

Above isolated diastereomeric salt is suspended in a water and water immiscible organic solvent and the resulting solution is treated with aqueous sodium bicarbonate, separate the organic layer, which is concentrated under reduced pressure to give residue. It is treated with solvent to give pure Eszopiclone. The solvent is selected from ethyl acetate, toluene, cyclohexane.

According to the present invention (R) or (S) Zopiclone is treated with acid followed by work-up to give 6-(5-chloropyridin-2-yl)-5-hydroxy-7-oxo-5,6-dihydro pyrrolo-[3,4-b]-pyrazine. The acid is selected from acetic acid, formic acid, hydrochloric acid, hydrobromic acid or mixtures thereof; According to our invention isolated 6-(5-chloropyridin-2-yl)-5-hydroxy-7-oxo-5,6-dihydro pyrrolo-[3,4-b]-pyrazine is further converted into Zopiclone by conventional method.

According to present invention the obtained Eszopiclone is having the enantiomeric purity about 95.0% to 99.5%.

Another embodiment of the present invention relates to process for the conversion of (R) or (S) Zopiclone to 6-(5-chloropyridin-2-yl)-5-hydroxy-7-oxo-5,6-dihydro pyrrolo-[3,4-b]-pyrazine of the intermediate which can be converted to racemic Zopiclone.

According to the present invention, (R) or (S) Zopiclone is treated with acid selected from acetic acid, formic acid, hydrochloric acid, hydrobromic acid or mixtures thereof; the resulting solution is heated between 50° to 70° C. followed by cooling and diluting with water to give 6-(5-chloropyridin-2-yl)-5-hydroxy-7-oxo-5,6-dihydro pyrrolo-[3,4-b]-pyrazine. This intermediate is used for the preparation of Zopiclone by conventional method.

While the present invention has been described in terms of its specific embodiments, certain modifications and equivalents will be apparent to those skilled in the art and are intended to be included within the scope of the present invention.

The invention is further illustrated with a few non-limiting examples

EXAMPLE-1

Preparation of 3-(5-chloropyridin-2-yl)-carbamoylpyrazine-2-carboxylic acid

2-Amino-5-chloro pyridine (171.2 g) was suspended in 800 ml toluene and mixture was heated to 48-52° C. Pyrazine-2,3-dicarboxylic acid anhydride (100 g) was added to the suspension at same temperature. The resulting reaction mixture was stirred for 2 hrs at 48-52° C. The reaction slurry was cooled to 20-25° C. and stirred for 30 min. The solid was filtered and washed with 100 ml toluene. The filtered solid was added to a mixture of 1000 ml water and 100 ml conc. HCl at 10-15° C. The solid was stirred for 60 min at 10-15° C. and filtered. The solid was slurred in 400 ml water, filtered and washed with 100 ml water. The solid was dried at 60-70° C. to yield 170 g of title compound.

EXAMPLE-2

Preparation of 6-(5-chloropyridin-2-yl)-5,7-dioxo-5,6-dihydropyrrolo-[3,4-b]-pyrazine 3-(5-Chloropyridin-2-yl)-carbamoylpyrazine-2-carboxylic acid (100 g) was suspended in 500 ml dichloromethane. The suspension was refluxed azeotropically for 60 min. The mixture was cooled to 25-30° C. and dimethyl formamide (2.6 gm) was added followed by addition of thionyl chloride (72 g) in 45-60 min at 25-30° C. The resulting mixture was refluxed till completion of reaction. The reaction mixture was concentrated to dryness at atmospheric pressure. Cooled the solid to 20-25° C. and 500 ml chilled water was added Cooled the slurry to 20-25° C. and stirred for 30 min. Slurry was filtered and washed with 200 ml water. The solid was dried at 60-70° C. to obtain 88 g of title compound.

EXAMPLE-3

Preparation of 6-(5-chloropyridin-2-yl)-5-hydroxy-7-oxo-5,6-dihydro pyrrolo-[3,4-b]-pyrazine 6-(5-Chloropyridin-2-yl)-5,7-dioxo-5,6-dihydropyrrolo-[3,4-b]-pyrazine (100g) was suspended in 900 ml water. The slurry was cooled to 0-5° C. and 100 ml (7.2%) of aqueous sodium borohydride solution stabilized with 0.1 g sodium hydroxide was added in 3 hrs under vigorous stirring. Reaction mixture was stirred at 0-5° C. for 4 to 5 hrs. After completion of reaction solid was filtered and washed with 2×300 ml water. The filtered solid was refluxed in 215 ml dichloromethane for 30 min and cooled to 25-30° C. The solid was filtered, washed with 100 ml dichloromethane and dried at 50-60° C. to obtain 82 g of title compound.

EXAMPLE-4

Preparation of 6-(5-chloropyridin-2-yl)-5-(4-methylpiperazin-1-yl)-carbonyloxy -7-oxo-5,6-dihydro-pyrrolo-[3,4-b]-pyrazine (Zopiclone)

Mixture of 400 ml dichloromethane, 100 ml dimethyl formamide, 6-(5-chloropyridin-2-yl)-5-hydroxy-7-oxo-5,6-dihydropyrrolo-[3,4-b]-pyrazine (100g) and N-methyl piperazine carbomoyl chloride hydrochloride (106.1 g) was cooled to 10-15° C. Calcium oxide (42.66 g) and dimethyl amino pyridine (2.5 g) were added to the mixture. Reaction mixture was warmed to 25-30° C. and stirred till completion of reaction. After completion of reaction, mixture was filtered and washed with 400 ml dichloromethane. The dichloromethane layer was concentrated at atmospheric pressure till dryness. 400 ml of methanol was added to residual solid and stirred for 60 min at 25-30° C. Slurry was cooled to 0-5° C. and stirred for 60 min at same temperature. Solid was filtered, washed with chilled methanol 2×25 ml and dried at 50-60° C. to obtain 126 g of racemic Zopiclone

EXAMPLE-5

Preparation of 6-(5-chloropyridin-2-yl)-5-(4-methylpiperazin-1-yl)-carbonyloxy-7-oxo-5,6-dihydropyrrolo-[3,4-b]-pyrazine D(+)-O,O'-dibenzoyltartaric acid salt Method I Mixture of acetonitrile 1200 ml, water 800 ml, 6-(5-chloropyridin-2-yl)-5-(4-methylpiperazin-1-yl)-carbonyloxy-7-oxo-5,6-dihydropyrrolo-[3,4-b]-pyrazine (Zopiclone) (100 g) and D(+)-O,O'-dibenzoyltartaric acid (90.3 g) was stirred for 2 hrs at 25-30° C. The mixture was heated to 75-80° C. till clear solution was obtained. The mixture was cooled slowly to 50° C. and stirred for 60 min at the same temperature. The mixture was further cooled slowly to 30-32° C. and solid obtained was filtered. The filtered solid was washed with 100 ml acetonitrile. The solid was dried at 60-65° C. to obtain 92 g of Zopiclone salt with chiral purity >99.0%

Method II:

Mixture of acetonitrile 1200 ml, water 800 ml, 6-(5-chloropyridin-2-yl)-5-(4-methyl piperazin-1-yl)-carbonyloxy-7-oxo-5,6-dihydropyrrolo-[3,4-b]-Pyrazine(Zopiclone) (100 g) and D(+)-O,O'-dibenzoyltartaric acid (90.3 g) was stirred for 2 hrs at 25-30° C. The mixture was heated to 75-80° C. till clear solution obtained. The mixture was cooled slowly to 50° C. and stirred for 60 min at the same temperature. The mixture was cooled slowly to 40° C. and stirred for 60 min. The mixture was further cooled slowly to 28-30° C. and stirred for 30 min at 28° C. Then the solid was filtered and washed with 100 ml acetonitrile. The solid was dried at 60-65° C. to obtain 90 g of Zopiclone with chiral purity ~97.0%

EXAMPLE-6

Preparation of [(9S)-8-(5-chloropyridin-2-yl)-7-oxo-2,5,8-triazabicyclo-[4.3.0]-nona-1,3,5-trien-9-yl]-4-methyl piperazine-1-carboxylate Mixture of ethyl acetate 1500 ml, 6-(5-chloropyridin-2-yl)-5-(4-methylpiperazin-1-yl)-carbonyloxy-7-oxo-5,6-dihydropyrrolo-[3,4-b]-pyrazine D(+)-O,O'-dibenzoyltartaric acid salt 100 g and water 250 ml was warmed to 40-42° C. Sodium bicarbonate (28.1 g) was added to the mixture and heated to 60-65° C. Reaction mixture was stirred for 30 min and organic layer was separated. The organic layer was washed with 200 ml water. The organic layer was treated with activated carbon (5 g) for 30 min at 60° C. Carbon was filtered over high flow and washed with 100 ml ethyl acetate. The filtrate was concentrated to 250 ml under mild vacuum at 50-55° C. The slurry was slowly cooled to 0-5° C. and stirred for 2 hrs at the same temperature. The solid was filtered and washed with 50 ml ethyl acetate. The solid was dried at 50-60° C. to obtain 44 g Eszopiclone with chiral purity >99.5%

Different Methods of Preparation of Enantiomerically Enriched Eszopiclone.

EXAMPLE-7

Method-I:

A Mixture of ethyl acetate 1500 ml, 6-(5-chloropyridin-2-yl)-5-(4-methylpiperazin-1-yl)-carbonyloxy-7-oxo-5,6-dihydropyrrolo-[3,4-b]-pyrazine D(+)-O,O'-dibenzoyltartaric acid salt 100 g (Chiral purity 99%) and water 250 ml was warmed to 40-42° C. Sodium bicarbonate (28.1 g) was added to the mixture and heated to 60-65° C. Reaction mixture was stirred for 30 min and organic layer was separated. The organic layer was washed with 200 ml water. The organic layer was treated with activated carbon (5 g) for 30 min at 60° C. Carbon was filtered over hyflo and washed with 100 ml ethyl acetate. The filtrate was concentrated to 800 ml under mild vacuum at 50-55° C. Racemic Zopiclone (1.3 g) was seeded to the filterate. The filterate was concentrated to 250 ml volume. The slurry was slowly cooled to -5° C. to -10° C. and stirred for 2 hrs at the same temperature The solid was filtered and washed with chilled 50 ml ethyl acetate (-10° C.). The solid was dried at 50-60° C. to obtain 44 g Eszopiclone with chiral purity ~99.1%

Method-II:

A Mixture of ethyl acetate 1500 ml, 6-(5-chloropyridin-2-yl)-5-(4-methylpiperazin-1-yl)-carbonyloxy-7-oxo-5,6-dihydropyrrolo-[3,4-b]-pyrazine D(+)-O,O'-dibenzoyltartaric acid salt 100 g (Chiral purity 99%) and water 250 ml was warmed to 40-42° C. Sodium bicarbonate (28.1 g) was added to the mixture and heated to 60-65° C. Reaction mixture was stirred for 30 min and organic layer was separated. The organic layer was washed with 200 ml water. The organic layer was treated with activated carbon (5 g) for 30 min at 60° C. Carbon was filtered over hyflo and washed with 100 ml ethyl acetate. The filtrate was concentrated to 800 ml under mild vacuum at 50-55° C. Zopiclone salt (1.3 g) was seeded to the filtrate. The filtrate was concentrated to ~250 ml volume. The slurry was slowly cooled to -5° C. to -10° C. and stirred for 2 hrs at the same temperature. The solid was filtered and washed with chilled 50 ml ethyl acetate (-10° C.). The solid was dried at 50-60° C. to obtain 44 g Eszopiclone with chiral purity ~99.1%

Method-III:

Mixture of ethyl acetate 1500 ml, 6-(5-chloropyridin-2-yl)-5-(4-methylpiperazin-1-yl)-carbonyloxy-7-oxo-5,6-dihydropyrrolo-[3,4-b]-Pyrazine D(+)-O,O'-dibenzoyltartaric acid salt 100 g (Chiral purity. 99%) and water 250 ml was warmed to 40-42° C. Sodium bicarbonate (28.1 g) was added to the mixture and heated to 60-65° C. Reaction mixture was stirred for 30 min and organic layer was separated. The organic layer was washed with 200 ml water. The organic layer was treated with activated carbon (5 g) for 30 min at 60° C. Carbon was filtered over hyflo and washed with 100 ml ethyl acetate. The filtrate was concentrated to 800 ml under mild vacuum at 50-55° C. (R)-Zopiclone (0.65 g) was seeded to the filtrate. The filtrate was concentrated to ~250 ml volume. The slurry was slowly cooled to -5° C. to -10° C. and stirred for 2hrs at the same temperature. The solid was filtered and washed with chilled 50 ml ethyl acetate (-10° C.) and then dried at 50-60° C. to obtain 44 g Eszopiclone with chiral purity ~99.1%

Method IV:

Mixture of dichloromethane 300 ml, 6-(5-chloropyridin-2-yl)-5-(4-methyl piperazin-1-yl)-carbonyloxy-7-oxo-5,6-dihydropyrrolo-[3,4-b]-pyrazine D(+)-O,O'-di benzoyltartaric acid salt 100 g (Chiral purity 99%)and water 250 ml was warmed to 35-37° C. Sodium bicarbonate (28.1 g) was added to the mixture and maintained at 35-37° C. Reaction mixture was stirred for 30-60 min and cooled to 25-30° C. Organic layer was separated. The organic layer was washed with 200 ml water and then treated with activated carbon (5 g) for 30 min at 20-25° C. Carbon was filtered over hyflo and washed with 100 ml dichloromethane. The filtrate was concentrated to 150 ml at atmospheric pressure. Zopiclone (1.3 g) was added to the mixture. Cyclohexane (600 ml) was added to residual solution at 25-30° C. in 60 min. The slurry was slowly cooled to 0° C. to 5° C. and stirred for 60 min at same temperature. The solid was filtered and washed with chilled 50 ml Cyclohexane (10° C.) and then dried at 50-60° C. to obtain 44 g Eszopiclone with chiral purity ~99.1%

Method V:

Mixture of dichloromethane 300 ml, 6-(5-chloropyridin-2-yl)-5-(4-methylpiperazin-1-yl)-carbonyloxy-7-oxo-5,6-dihydropyrrolo-[3,4-b]-pyrazine D (+)-O,O'-dibenzoyltartaric acid salt 100 g (Chiral purity 97%) and water 250 ml was warmed to 35-37° C. Sodium bicarbonate (28.1 g) was added to the mixture and maintained at 35-37° C. Reaction mixture was stirred for 30-60 min and cooled to 25-30° C. Organic layer was separated. The organic layer was washed with 200 ml water and then with activated carbon (5 g) for 30 min at 20-25° C. Carbon was filtered over hyflo and washed with 100 ml dichloromethane. The filtrate was concentrated to 150 ml at atmospheric pressure. Cyclohexane (600 ml) was added to residual solution at 25-30° C. in 60 min. The slurry was slowly cooled to 0 to 5° C. and stirred for 60 min at same temperature. The solid was filtered and washed with chilled 50 ml Cyclohexane (10° C.) and then dried at 50-60° C. to obtained 44 g Eszopiclone with chiral purity ~97%

Method VI:

Stirred the suspension of D.M. Water (1000 ml) and 6-(5-chloropyridin-2-yl)-5-(4-methylpiperazin-1-yl)-carbonyloxy-7-oxo-5,6-dihydropyrrolo-[3,4-b]-pyrazine D(+)-O,O'-dibenzoyltartaric acid salt 100 g (Chiral purity 99%) at 25-30° C. Prefiltered sodium bicarbonate solution (28.1 g sodium bicarbonate+500 ml D.M. Water) was added in 1-2 hrs at 25-30° C. The resulting slurry was stirred for 2 hrs at 25-30° C. and filtered. The solid was washed with D.M. Water (2×200 ml) at 25-30° C. The solid was dried under vacuum at 50-60° C. till moisture content NMT 0.2% to obtain 49 g Eszopiclone with chiral purity of ~99.3%

Method VII:

Stirred the suspension of D.M. Water (1000 ml) and 6-(5-chloropyridin-2-yl)-5-(4-methylpiperazin-1-yl)-carbonyloxy-7-oxo-5,6-dihydropyrrolo-[3,4-b]-Pyrazine D (+)-O,O'-dibenzoyltartaric acid salt 100 g (Chiral purity 97%) at 25-30°. Pre filtered sodium bicarbonate solution (28.1 g sodium bicarbonate+500 ml D.M. Water) was added in 1-2 hrs at 25-30° C. The resulting slurry was stirred for 2 hrs at 25-30° C. and filtered. The solid was washed with DM Water (2×200 ml) at 25-30° C. The solid was dried under vacuum at 50-60° C. till moisture content NMT 0.2%. To obtained 49 g Eszopiclone with chiral purity ~97%

EXAMPLE-8

Process for the Conversion of R-Enantiomer of Zopiclone to 6-(5-chloropyridin-2-yl)-5-hydroxy-7-oxo-5,6-dihydropyrrolo-[3,4-b]-pyrazine Concentrated the mother liquor (acetonitrile water mixture) of Example-4 to 250 ml under reduced pressure at below 70° C. Cooled the mixture to 25-30° C., added 300 ml water to the residue followed by 300 ml dichloromethane. Stirred the mixture for 15 min and sodium bicarbonate (30 g) was added to the mixture. The mixture was stirred for 30 min at 25-30° C., dichloromethane was separated. Solvent was concentrated at atmospheric pressure to dryness. Finally traces of dichloromethane were removed under reduced pressure. Formic acid 50 ml was added to the residue followed by 28 ml conc.HCl. The resulting reaction mixture was heated to 64-68° C. and stirred for 3 hrs at the same temperature. Cooled the mixture to 25-30° C. and 200 ml water was added to the reaction mixture. Cooled the slurry to 0-5° C. and stirred for 60 min at same temperature. The solid was filtered and washed with 100 ml water at 0-5° C. Dried the solid at 60-65° C. to obtain 28 g of 6-(5-chloropyridin-2-yl)-5-hydroxy-7-oxo-5,6-dihydropyrrolo-[3,4-b]-Pyrazine of HPLC purity >99%.

We claim:

1. A process for the preparation of racemic Zopiclone, comprising the step of condensing 6-(5-chloropyrid-2-yl)-5-hydroxy-7-oxo-5,6-dihydropyrrolo[3,4-b]pyrazine with 1-chlorocarbonyl-4-methylpiperazine in the presence of dimethylaminopyridine, and at least one alkaline earth metal carbonate, hydroxide or oxide in a solvent medium to give racemic Zopiclone.

2. A process for the preparation of racemic Zopiclone according to claim 1, wherein the alkaline earth metal carbonate is selected from the, group consisting of magnesium carbonate and calcium carbonate; the alkaline earth metal hydroxide is selected from the group consisting of magnesium hydroxide and calcium hydroxide; and the alka inc earth metal oxide is selected from the group consisting of magnesium oxide calcium oxide.

3. A process for the preparation of racemic Zopiclone according to claim 1, wherein the solvent is selected from the group consisting of toluene, dichloromethane, dichloroethane, ethyl acetate, tetrahydrofuran, N,N'-dimethylformamide, N,N'-dimethylacetamide, dimethyl sulfoxide and mixtures thereof.

4. A process for the preparation of enantiomerically enriched Zopiclone, comprising the steps of:
(a) condensing 6-(5-chloropyrid-2-yl)-5-hydroxy-7-oxo-5,6-dihydropyrrolo[3,4-b]pyrazine with 1-chlorocarbonyl-4-methylpiperazine in the presence of dimethylaminopyridine and at least one alkaline earth metal carbonate, hydroxide or oxide in a solvent medium to give racemic Zopiclone, and
(b) reacting the obtained racemic Zopiclone with an optically active acid in a mixture of water and at least one water miscible organic solvent and recovering (R)-Zopiclone or (S)-Zopiclone.

5. A process for the preparation of (S)-Zopiclone according to claim 4, wherein the at least one water miscible organic solvent is selected from the group consisting of ketones, nitriles and aprotic polar solvents.

6. A process for the preparation of (S)-Zopiclone according to claim 5, wherein the ketone solvent is acetone, the nitrile solvent is selected from the group consisting of acetonitrile and propionitrile, and the aprotic polar solvent is selected from the group consisting of N,N'-dimethylformamide, N,N'-dimethylacetamide, and dimethyl sulfoxide.

7. A process for the preparation of (S)-Zopiclone according to claim 4, wherein the optically active acid is selected from the group consisting of D-(+)-O,O'-dibenzoyltartaric acid, D-(+)-O,O'-p-toluyldibenzoyltartaric acid, and D-(+)-mandelic acid.

* * * * *